(12) United States Patent
Griffin (10) Patent No.: US 11,406,404 B2
(45) Date of Patent: Aug. 9, 2022

(54) CLOT REMOVAL DISTAL PROTECTION METHODS

(71) Applicant: Cerus Endovascular Limited, Oxford (GB)

(72) Inventor: Stephen Griffin, Fremont, CA (US)

(73) Assignee: Cerus Endovascular Limited, Oxford (GB)

( * ) Notice: Subject to any disclaimer, the term of this patent is extended or adjusted under 35 U.S.C. 154(b) by 328 days.

(21) Appl. No.: 16/796,788

(22) Filed: Feb. 20, 2020

(65) Prior Publication Data
US 2021/0259719 A1    Aug. 26, 2021

(51) Int. Cl.
*A61F 2/01* (2006.01)
*A61B 17/221* (2006.01)

(52) U.S. Cl.
CPC ........... *A61B 17/221* (2013.01); *A61F 2/013* (2013.01); *A61B 2017/2215* (2013.01); *A61B 2217/005* (2013.01)

(58) Field of Classification Search
CPC ........... A61B 17/221; A61B 17/22031; A61B 2017/2212; A61B 2017/2215; A61B 2017/2217; A61B 2217/005; A61F 2/013; A61F 2/014
See application file for complete search history.

(56) References Cited

U.S. PATENT DOCUMENTS

| | | |
|---|---|---|
| 2,849,002 A | 8/1958 | Oddo |
| 3,480,017 A | 11/1969 | Shute |
| 4,364,392 A | 12/1982 | Strother et al. |
| 4,395,806 A | 8/1983 | Wonder et al. |
| 4,545,367 A | 10/1985 | Tucci |
| 4,836,204 A | 6/1989 | Landymore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |

(Continued)

FOREIGN PATENT DOCUMENTS

| | | |
|---|---|---|
| CA | 2946078 | 11/2015 |
| CN | 102940514 | 3/2013 |

(Continued)

OTHER PUBLICATIONS

US 9,034,010 B2, 05/2015, Amin (withdrawn)

(Continued)

*Primary Examiner* — Wade Miles
(74) *Attorney, Agent, or Firm* — Fish & Richardson P.C.

(57) ABSTRACT

Provided herein are methods for protecting distal vessels from emboli during aspiration, the method comprising delivery and deployment of an emboli protection device which is advanced and placed distally relative to the clot burden and thus deep in the neurovascular bed until the device, once deployed, fully opposes a vessel wall creating a circumferential seal across the vessel. The methods utilizing the emboli protection device protect distal vasculature from vulnerable clot emboli which become dislodged during clot removal and/or aspiration and trapped in the emboli protection device.

18 Claims, 4 Drawing Sheets

(56) References Cited

U.S. PATENT DOCUMENTS

| | | | |
|---|---|---|---|
| 5,423,829 | A | 6/1995 | Pham et al. |
| 5,496,277 | A | 3/1996 | Termin et al. |
| 5,624,449 | A | 4/1997 | Pham et al. |
| 5,733,294 | A | 3/1998 | Forber et al. |
| 5,891,128 | A | 4/1999 | Gia et al. |
| 5,928,260 | A | 7/1999 | Chin et al. |
| 6,007,573 | A | 12/1999 | Wallace et al. |
| 6,024,756 | A | 2/2000 | Pham |
| 6,080,191 | A | 6/2000 | Thaler |
| 6,096,021 | A | 8/2000 | Helm et al. |
| 6,113,609 | A | 9/2000 | Adams |
| 6,123,714 | A | 9/2000 | Gia et al. |
| 6,152,144 | A | 11/2000 | Lesh et al. |
| 6,168,579 | B1 * | 1/2001 | Tsugita ............ A61B 17/12136 604/509 |
| 6,168,622 | B1 | 1/2001 | Mazzocchi |
| 6,221,086 | B1 | 4/2001 | Forber |
| 6,270,515 | B1 | 8/2001 | Linden et al. |
| 6,315,787 | B1 | 11/2001 | Tsugita et al. |
| 6,334,048 | B1 | 12/2001 | Edvardsson et al. |
| 6,419,686 | B1 | 7/2002 | McLeod et al. |
| 6,454,780 | B1 | 9/2002 | Wallace |
| 6,463,317 | B1 | 10/2002 | Kucharczyk et al. |
| 6,506,204 | B2 | 1/2003 | Mazzocchi |
| 6,527,919 | B1 | 3/2003 | Roth |
| 6,547,804 | B2 | 4/2003 | Porter et al. |
| 6,551,303 | B1 | 4/2003 | Tassel et al. |
| 6,569,190 | B2 | 5/2003 | Whalen, II et al. |
| 6,589,230 | B2 | 7/2003 | Gia et al. |
| 6,589,256 | B2 | 7/2003 | Forber |
| 6,605,102 | B1 | 8/2003 | Mazzocchi et al. |
| 6,620,152 | B2 | 9/2003 | Guglielmi |
| 6,663,068 | B2 | 12/2003 | Huang |
| 6,669,719 | B2 | 12/2003 | Wallace et al. |
| 6,669,721 | B1 | 12/2003 | Bose et al. |
| 6,689,159 | B2 | 2/2004 | Lau et al. |
| 6,780,196 | B2 | 8/2004 | Chin et al. |
| 6,811,560 | B2 | 11/2004 | Jones |
| 6,833,003 | B2 | 12/2004 | Jones et al. |
| 6,855,154 | B2 | 2/2005 | Abdel-Gawwad |
| 6,949,116 | B2 | 9/2005 | Solymar et al. |
| 6,953,472 | B2 | 10/2005 | Palmer |
| 7,044,134 | B2 | 5/2006 | Khairkhahan et al. |
| 7,093,527 | B2 | 8/2006 | Rapaport et al. |
| 7,128,073 | B1 | 10/2006 | Burg et al. |
| 7,128,736 | B1 | 10/2006 | Abrams et al. |
| 7,152,605 | B2 | 12/2006 | Khairkhahan et al. |
| 7,195,636 | B2 | 3/2007 | Avellanet et al. |
| 7,229,454 | B2 | 6/2007 | Tran et al. |
| 7,229,461 | B2 | 6/2007 | Chin et al. |
| 7,232,461 | B2 | 6/2007 | Ramer |
| 7,306,622 | B2 | 12/2007 | Jones |
| 7,371,249 | B2 | 5/2008 | Douk et al. |
| 7,410,482 | B2 | 8/2008 | Murphey et al. |
| 7,572,288 | B2 | 8/2009 | Cox |
| 7,597,704 | B2 | 10/2009 | Frazier et al. |
| 7,695,488 | B2 | 4/2010 | Berenstein et al. |
| 7,713,264 | B2 | 5/2010 | Murphy |
| 7,722,641 | B2 | 5/2010 | Burg et al. |
| 7,744,652 | B2 | 6/2010 | Morsi |
| 7,828,818 | B2 | 11/2010 | Zang et al. |
| 7,892,254 | B2 | 2/2011 | Klint |
| 8,034,061 | B2 | 10/2011 | Amplatz et al. |
| 8,066,757 | B2 | 11/2011 | Ferrera |
| 8,075,585 | B2 | 12/2011 | Lee et al. |
| 8,080,032 | B2 | 12/2011 | Burg et al. |
| 8,088,140 | B2 | 1/2012 | Ferrera |
| 8,142,456 | B2 | 3/2012 | Rosqueta et al. |
| 8,221,483 | B2 | 7/2012 | Ford et al. |
| 8,252,040 | B2 | 8/2012 | Cox |
| 8,261,648 | B1 | 9/2012 | Marchand et al. |
| 8,262,692 | B2 | 9/2012 | Rudakov |
| 8,267,923 | B2 | 9/2012 | Murphy |
| 8,361,106 | B2 | 1/2013 | Solar et al. |
| 8,361,138 | B2 | 1/2013 | Adams |
| 8,372,114 | B2 | 2/2013 | Hines |
| 8,398,671 | B2 | 3/2013 | Chen |
| 8,430,012 | B1 | 4/2013 | Marchand et al. |
| 8,454,633 | B2 | 6/2013 | Amplatz et al. |
| 8,470,013 | B2 | 6/2013 | Duggal et al. |
| 8,500,751 | B2 | 8/2013 | Rudakov et al. |
| 8,523,897 | B2 | 9/2013 | Burg et al. |
| 8,535,343 | B2 | 9/2013 | Burg et al. |
| 8,545,514 | B2 | 10/2013 | Ferrera |
| 8,562,667 | B2 | 10/2013 | Cox |
| 8,574,262 | B2 | 11/2013 | Ferrera |
| 8,585,713 | B2 | 11/2013 | Ferrera |
| 8,597,320 | B2 | 12/2013 | Sepetka |
| 8,663,273 | B2 | 3/2014 | Khairkhahan |
| 8,696,701 | B2 | 4/2014 | Becking |
| 8,715,312 | B2 | 5/2014 | Burke |
| 8,715,316 | B1 | 5/2014 | Janardhan et al. |
| 8,747,453 | B2 | 6/2014 | Amplatz |
| 8,771,294 | B2 | 7/2014 | Sepetka |
| 8,834,519 | B2 | 9/2014 | Van Der Burg |
| 8,926,680 | B2 | 1/2015 | Ferrera |
| 8,945,172 | B2 | 2/2015 | Ferrera |
| 9,034,054 | B2 | 5/2015 | Gerberding |
| 9,039,724 | B2 | 5/2015 | Amplatz et al. |
| 9,060,077 | B2 | 6/2015 | Sayama |
| 9,060,777 | B1 | 6/2015 | Wallace |
| 9,078,658 | B2 | 7/2015 | Hewitt |
| 9,107,670 | B2 | 8/2015 | Hannes |
| 9,138,213 | B2 | 9/2015 | Amin |
| 9,161,758 | B2 | 10/2015 | Figulla |
| 9,168,043 | B2 | 10/2015 | Van Der Burg |
| 9,179,918 | B2 | 11/2015 | Levy |
| 9,186,487 | B2 | 11/2015 | Dubrul et al. |
| 9,198,668 | B2 | 12/2015 | Theobald |
| 9,198,670 | B2 | 12/2015 | Hewitt |
| 9,198,687 | B2 | 12/2015 | Fulkerson |
| 9,220,522 | B2 | 12/2015 | Fulkerson |
| 9,259,337 | B2 | 2/2016 | Cox |
| 9,271,736 | B2 | 3/2016 | Heipl |
| 9,295,473 | B2 | 3/2016 | Hewitt |
| 9,307,998 | B2 | 4/2016 | Chin |
| 9,314,326 | B2 | 4/2016 | Wallace |
| 9,387,098 | B2 | 7/2016 | Ferrera |
| 9,474,517 | B2 | 10/2016 | Amin |
| 9,492,174 | B2 | 11/2016 | Hewitt |
| 9,498,604 | B2 | 11/2016 | Dubrul |
| 9,532,772 | B2 | 1/2017 | Moszner |
| 9,539,122 | B2 | 1/2017 | Burke |
| 9,545,300 | B2 | 1/2017 | Cully |
| 9,572,698 | B2 | 2/2017 | Franano |
| 9,597,087 | B2 | 3/2017 | Marchand |
| 9,622,770 | B2 | 4/2017 | Trapp |
| 9,629,635 | B2 | 4/2017 | Hewitt |
| 9,795,400 | B2 | 10/2017 | Davidson |
| 9,826,980 | B2 | 11/2017 | Figulla |
| 9,839,430 | B2 | 12/2017 | Willems |
| 9,861,467 | B2 | 1/2018 | Cully |
| 9,877,726 | B2 | 1/2018 | Liu |
| 9,918,720 | B2 | 3/2018 | Marchand |
| 9,943,299 | B2 | 4/2018 | Khairkhahan |
| 9,955,976 | B2 | 5/2018 | Hewitt |
| 9,962,146 | B2 | 5/2018 | Hebert |
| 9,980,733 | B2 | 5/2018 | Badruddin |
| 10,028,745 | B2 | 7/2018 | Morsi |
| 10,028,747 | B2 | 7/2018 | Connor |
| 10,076,399 | B2 | 9/2018 | Davidson |
| 10,123,803 | B2 | 11/2018 | Ferrera et al. |
| 10,130,372 | B2 | 11/2018 | Griffin |
| 10,136,896 | B2 | 11/2018 | Hewitt et al. |
| 10,159,490 | B2 | 12/2018 | Wallace et al. |
| 10,231,722 | B2 | 3/2019 | Hebert et al. |
| 10,238,393 | B2 | 3/2019 | Marchand et al. |
| 10,265,075 | B2 | 4/2019 | Porter et al. |
| 10,278,705 | B2 | 5/2019 | Amin et al. |
| 10,285,678 | B2 | 5/2019 | Hebert et al. |
| 10,285,679 | B2 | 5/2019 | Hebert et al. |
| 10,285,711 | B2 | 5/2019 | Griffin |
| 10,299,775 | B2 | 5/2019 | Hebert et al. |
| 10,342,546 | B2 | 7/2019 | Sepetka et al. |

(56) References Cited

U.S. PATENT DOCUMENTS

| | | |
|---|---|---|
| 10,383,635 B2 | 8/2019 | Wallace et al. |
| 10,398,441 B2 | 9/2019 | Warner et al. |
| 10,398,444 B2 | 9/2019 | Morsi |
| 10,433,851 B2 | 10/2019 | Adams et al. |
| 10,478,194 B2 | 11/2019 | Rhee et al. |
| 10,499,939 B2 | 12/2019 | Davidson |
| 10,537,451 B2 | 1/2020 | Franano et al. |
| 10,543,015 B2 | 1/2020 | Walzman |
| 10,543,115 B2 | 1/2020 | Franano et al. |
| 10,548,607 B2 | 2/2020 | Walzman |
| 10,561,411 B1 | 2/2020 | Cole et al. |
| 10,561,441 B2 | 2/2020 | Walzman |
| 10,603,070 B2 | 3/2020 | Walzman |
| 10,610,231 B2 | 4/2020 | Marchand et al. |
| 10,617,428 B2 | 4/2020 | Walzman |
| 10,653,403 B2 | 5/2020 | Hebert et al. |
| 10,716,549 B2 | 7/2020 | Keillor |
| 10,716,573 B2 | 7/2020 | Connor |
| 10,716,574 B2 | 7/2020 | Lorenzo et al. |
| 10,729,447 B2 | 8/2020 | Shimizu et al. |
| 10,743,852 B2 | 8/2020 | Moszner et al. |
| 10,743,884 B2 | 8/2020 | Lorenzo |
| 10,751,065 B2 | 8/2020 | Soto Del Valle et al. |
| 10,751,066 B2 | 8/2020 | Lorenzo |
| 10,772,747 B2 | 9/2020 | Fischer et al. |
| 10,808,341 B2 | 10/2020 | Koppe |
| 10,813,645 B2 | 10/2020 | Hewitt et al. |
| 10,835,257 B2 | 11/2020 | Ferrera et al. |
| 10,856,879 B2 | 12/2020 | Badruddin et al. |
| 10,856,880 B1 | 12/2020 | Badruddin et al. |
| 10,869,672 B2 | 12/2020 | Griffin |
| 10,881,413 B2 | 1/2021 | Merritt et al. |
| 10,888,333 B2 | 1/2021 | Kealey et al. |
| 10,905,430 B2 | 2/2021 | Lorenzo et al. |
| 10,925,612 B2 | 2/2021 | Wallace et al. |
| 10,939,914 B2 | 3/2021 | Hewitt et al. |
| 10,939,915 B2 | 3/2021 | Gorochow et al. |
| 10,952,739 B2 | 3/2021 | Plaza et al. |
| 10,959,735 B2 | 3/2021 | Morsi |
| 10,980,545 B2 | 4/2021 | Bowman et al. |
| 11,058,430 B2 | 7/2021 | Gorochow et al. |
| 2001/0041900 A1 | 11/2001 | Callister |
| 2002/0082638 A1 | 6/2002 | Porter et al. |
| 2002/0143349 A1 | 10/2002 | Gifford, II et al. |
| 2002/0169473 A1 | 11/2002 | Sepetka |
| 2002/0188314 A1 | 12/2002 | Anderson et al. |
| 2003/0055451 A1 | 3/2003 | Jones et al. |
| 2003/0120337 A1 | 6/2003 | Tassel et al. |
| 2003/0171739 A1 | 9/2003 | Murphy et al. |
| 2003/0176884 A1 | 9/2003 | Berrada |
| 2003/0181927 A1 | 9/2003 | Wallace |
| 2003/0195553 A1 | 10/2003 | Wallace et al. |
| 2003/0220667 A1 | 11/2003 | Van Der Burg |
| 2004/0034366 A1 | 2/2004 | Burg et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Tassel et al. |
| 2004/0133222 A1 | 8/2004 | Tran et al. |
| 2004/0167597 A1 | 8/2004 | Costantino |
| 2004/0172056 A1 | 9/2004 | Guterman |
| 2004/0181253 A1 | 9/2004 | Sepetka |
| 2004/0193246 A1 | 9/2004 | Ferrera |
| 2004/0254594 A1 | 12/2004 | Alfaro |
| 2004/0260332 A1 | 12/2004 | Dubrul |
| 2005/0021016 A1 | 1/2005 | Malecki et al. |
| 2005/0119684 A1 | 6/2005 | Guterman |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman |
| 2006/0116709 A1 | 6/2006 | Sepetka |
| 2006/0116713 A1 | 6/2006 | Sepetka |
| 2006/0155323 A1 | 7/2006 | Porter et al. |
| 2006/0155367 A1 | 7/2006 | Hines |
| 2006/0167494 A1 | 7/2006 | Suddaby |
| 2006/0206199 A1 | 9/2006 | Churchwell et al. |
| 2007/0043391 A1 | 2/2007 | Moszner et al. |
| 2007/0106311 A1 | 5/2007 | Wallace et al. |
| 2007/0150045 A1 | 6/2007 | Ferrera |
| 2007/0173928 A1 | 7/2007 | Morsi |
| 2007/0198075 A1 | 8/2007 | Levy |
| 2007/0203567 A1 | 8/2007 | Levy |
| 2007/0208376 A1 | 9/2007 | Meng |
| 2007/0225760 A1 | 9/2007 | Moszner |
| 2007/0270902 A1 | 11/2007 | Slazas |
| 2007/0288083 A1 | 12/2007 | Hines |
| 2008/0045995 A1 | 2/2008 | Guterman |
| 2008/0097401 A1 | 4/2008 | Trapp |
| 2008/0097495 A1 | 4/2008 | Feller, III et al. |
| 2008/0147100 A1 | 6/2008 | Wallace |
| 2008/0221600 A1 | 9/2008 | Dieck et al. |
| 2009/0082803 A1 | 3/2009 | Adams |
| 2009/0099647 A1 | 4/2009 | Glimsdale |
| 2009/0192455 A1 | 7/2009 | Ferrera |
| 2009/0209855 A1 | 8/2009 | Drilling et al. |
| 2009/0228029 A1 | 9/2009 | Lee |
| 2009/0281557 A1 | 11/2009 | Sander et al. |
| 2009/0297582 A1 | 12/2009 | Meyer |
| 2009/0318941 A1 | 12/2009 | Sepetka |
| 2010/0069948 A1 | 3/2010 | Veznedaroglu et al. |
| 2010/0174309 A1 | 7/2010 | Fulkerson |
| 2010/0217187 A1 | 8/2010 | Fulkerson |
| 2010/0256600 A1 | 10/2010 | Ferrera |
| 2010/0268204 A1 | 10/2010 | Tieu et al. |
| 2010/0318097 A1 | 12/2010 | Ferrera |
| 2011/0022149 A1 | 1/2011 | Cox |
| 2011/0040319 A1* | 2/2011 | Fulton, III ............... A61F 2/82 |
| | | 623/1.15 |
| 2011/0046658 A1 | 2/2011 | Connor et al. |
| 2011/0054519 A1 | 3/2011 | Neuss |
| 2011/0082491 A1 | 4/2011 | Sepetka |
| 2011/0152993 A1 | 6/2011 | Marchand et al. |
| 2011/0160763 A1 | 6/2011 | Ferrera et al. |
| 2011/0190797 A1 | 8/2011 | Fulkerson |
| 2011/0202085 A1 | 8/2011 | Loganathan |
| 2011/0264132 A1 | 10/2011 | Strauss |
| 2011/0319926 A1 | 12/2011 | Becking et al. |
| 2011/0319978 A1 | 12/2011 | Schaffer |
| 2012/0016406 A1 | 1/2012 | Ferrera |
| 2012/0041460 A1 | 2/2012 | Ferrera |
| 2012/0041475 A1 | 2/2012 | Ferrera |
| 2012/0071911 A1 | 3/2012 | Sadasivan |
| 2012/0150147 A1 | 6/2012 | Leynov |
| 2012/0165919 A1 | 6/2012 | Cox |
| 2012/0172973 A1 | 7/2012 | Deckard et al. |
| 2012/0271337 A1 | 10/2012 | Figulla et al. |
| 2012/0277788 A1 | 11/2012 | Cattaneo |
| 2012/0283768 A1 | 11/2012 | Cox et al. |
| 2012/0330341 A1 | 12/2012 | Becking et al. |
| 2012/0330347 A1 | 12/2012 | Becking |
| 2013/0035628 A1* | 2/2013 | Garrison ............... A61M 1/82 |
| | | 604/9 |
| 2013/0035712 A1 | 2/2013 | Theobald et al. |
| 2013/0066357 A1 | 3/2013 | Aboytes et al. |
| 2013/0066360 A1 | 3/2013 | Becking |
| 2013/0066413 A1 | 3/2013 | Jin |
| 2013/0090682 A1 | 4/2013 | Bachman et al. |
| 2013/0123830 A1 | 5/2013 | Becking |
| 2013/0165967 A1 | 6/2013 | Amin |
| 2013/0190800 A1 | 7/2013 | Murphy |
| 2013/0197622 A1 | 8/2013 | Mitra et al. |
| 2013/0245667 A1 | 9/2013 | Marchand |
| 2013/0274862 A1 | 10/2013 | Cox |
| 2013/0274866 A1 | 10/2013 | Cox |
| 2013/0274868 A1 | 10/2013 | Cox et al. |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0052233 A1 | 2/2014 | Cox |
| 2014/0163609 A1 | 6/2014 | Solem |
| 2014/0172001 A1 | 6/2014 | Becking et al. |
| 2014/0200607 A1 | 7/2014 | Sepetka et al. |

(56) References Cited

U.S. PATENT DOCUMENTS

| | | |
|---|---|---|
| 2014/0257360 A1 | 9/2014 | Keillor |
| 2014/0257374 A1 | 9/2014 | Heisei et al. |
| 2014/0343602 A1 | 11/2014 | Cox |
| 2014/0358178 A1 | 12/2014 | Hewitt et al. |
| 2015/0105817 A1 | 4/2015 | Marchand |
| 2015/0133990 A1 | 5/2015 | Davidson |
| 2015/0150563 A1 | 6/2015 | Marchand |
| 2015/0250628 A1 | 9/2015 | Monstadt |
| 2015/0272589 A1 | 10/2015 | Lorenzo |
| 2015/0351770 A1 | 12/2015 | Fulton, III |
| 2015/0351775 A1 | 12/2015 | Fulton, III |
| 2016/0106437 A1 | 4/2016 | Van Der Burg |
| 2016/0113662 A1* | 4/2016 | Kobayashi ........... A61B 17/221 606/127 |
| 2016/0120551 A1 | 5/2016 | Connor |
| 2016/0174991 A1 | 6/2016 | Chin |
| 2016/0206321 A1 | 7/2016 | Connor |
| 2016/0213380 A1 | 7/2016 | O'Brien |
| 2016/0249934 A1 | 9/2016 | Hewitt et al. |
| 2016/0249935 A1 | 9/2016 | Hewitt et al. |
| 2016/0345979 A1 | 12/2016 | Adams et al. |
| 2017/0128077 A1 | 5/2017 | Hewitt et al. |
| 2017/0156733 A1 | 6/2017 | Becking |
| 2017/0156734 A1 | 6/2017 | Griffin |
| 2017/0172581 A1 | 6/2017 | Bose |
| 2018/0125500 A1 | 5/2018 | Connor |
| 2018/0140305 A1 | 5/2018 | Connor |
| 2018/0193024 A1 | 7/2018 | Walzman |
| 2018/0193043 A1* | 7/2018 | Marchand ............... A61F 2/013 |
| 2018/0206848 A1 | 7/2018 | Walzman |
| 2018/0206851 A1 | 7/2018 | Walzman |
| 2018/0214158 A1 | 8/2018 | Walzman |
| 2018/0333248 A1 | 11/2018 | Davidson |
| 2019/0008522 A1 | 1/2019 | Lorenzo |
| 2019/0053810 A1 | 2/2019 | Griffin |
| 2019/0059909 A1 | 2/2019 | Griffin |
| 2019/0110796 A1 | 4/2019 | Jayaraman |
| 2019/0183519 A1* | 6/2019 | Imai ..................... A61F 2/013 |
| 2019/0209146 A1 | 7/2019 | Hebert |
| 2019/0209178 A1 | 7/2019 | Richter |
| 2019/0216467 A1 | 7/2019 | Goyal |
| 2019/0223876 A1 | 7/2019 | Badruddin |
| 2019/0223881 A1 | 7/2019 | Hewitt |
| 2019/0231328 A1 | 8/2019 | Hebert |
| 2019/0262002 A1 | 8/2019 | Benjamin |
| 2019/0269414 A1 | 9/2019 | Griffin |
| 2019/0274691 A1 | 9/2019 | Sepetka |
| 2019/0336132 A1 | 11/2019 | Warner |
| 2019/0343533 A1 | 11/2019 | Costalat |
| 2019/0357914 A1 | 11/2019 | Gorochow |
| 2019/0365472 A1 | 12/2019 | Connor |
| 2019/0374228 A1 | 12/2019 | Wallace |
| 2019/0380718 A1 | 12/2019 | Morsi |
| 2019/0388108 A1 | 12/2019 | Ferrera |
| 2020/0029973 A1 | 1/2020 | Walzman |
| 2020/0038032 A1 | 2/2020 | Rhee |
| 2020/0038035 A1 | 2/2020 | Griffin |
| 2020/0054344 A1 | 2/2020 | Connor |
| 2020/0060702 A1 | 2/2020 | Davidson |
| 2020/0069313 A1 | 3/2020 | Xu |
| 2020/0093499 A1 | 3/2020 | Lorenzo |
| 2020/0100795 A1 | 4/2020 | Connor |
| 2020/0113576 A1 | 4/2020 | Gorochow |
| 2020/0138422 A1 | 5/2020 | Hebert |
| 2020/0155333 A1 | 5/2020 | Franano |
| 2020/0163784 A1 | 5/2020 | Franano |
| 2020/0187952 A1 | 6/2020 | Walsh |
| 2020/0187978 A1 | 6/2020 | Walzman |
| 2020/0253766 A1 | 8/2020 | Walzman |
| 2020/0268365 A1 | 8/2020 | Hebert |
| 2020/0281603 A1 | 9/2020 | Marchand |
| 2020/0289124 A1 | 9/2020 | Rangwala |
| 2020/0289125 A1 | 9/2020 | Dholakia |
| 2020/0289126 A1 | 9/2020 | Hewitt |
| 2020/0305886 A1 | 10/2020 | Soto Del |
| 2020/0323534 A1 | 10/2020 | Shimizu |
| 2020/0337710 A1 | 10/2020 | Lorenzo |
| 2020/0340154 A1 | 10/2020 | Köppe |
| 2020/0345376 A1 | 11/2020 | Fulton, III |
| 2020/0367894 A1 | 11/2020 | Pereira |
| 2020/0367896 A1 | 11/2020 | Zaidat |
| 2020/0367897 A1 | 11/2020 | Wolfe |
| 2020/0367904 A1 | 11/2020 | Becking |
| 2020/0375606 A1 | 12/2020 | Lorenzo |
| 2020/0375607 A1 | 12/2020 | Soto Del Valle |
| 2020/0390455 A1* | 12/2020 | Nguyen ................. A61L 29/02 |
| 2020/0397447 A1 | 12/2020 | Lorenzo |
| 2020/0405347 A1 | 12/2020 | Walzman |
| 2021/0007755 A1 | 1/2021 | Lorenzo |
| 2021/0022765 A1 | 1/2021 | Walzman |
| 2021/0045750 A1 | 2/2021 | Wolfe |
| 2021/0068842 A1 | 3/2021 | Griffin |
| 2021/0077116 A1 | 3/2021 | Ferrera |
| 2021/0106337 A1 | 4/2021 | Hewitt |
| 2021/0128160 A1 | 5/2021 | Li |
| 2021/0128161 A1 | 5/2021 | Nageswaran |
| 2021/0128162 A1 | 5/2021 | Rhee |
| 2021/0128165 A1 | 5/2021 | Pulugurtha |
| 2021/0128166 A1 | 5/2021 | Kealey |
| 2021/0128167 A1 | 5/2021 | Patel |
| 2021/0128168 A1 | 5/2021 | Nguyen |
| 2021/0128169 A1 | 5/2021 | Li |
| 2021/0129275 A1 | 5/2021 | Nguyen |
| 2021/0145449 A1 | 5/2021 | Gorochow |
| 2021/0153871 A1 | 5/2021 | Griffin |
| 2021/0186518 A1 | 6/2021 | Gorochow et al. |
| 2021/0251635 A1 | 8/2021 | Soto Del Valle et al. |

FOREIGN PATENT DOCUMENTS

| | | |
|---|---|---|
| CN | 103099652 | 5/2013 |
| CN | 104168843 | 11/2014 |
| CN | 104958087 | 10/2015 |
| CN | 204931771 | 1/2016 |
| DE | 102008028308 | 4/2009 |
| DE | 102008015781 | 9/2011 |
| DE | 102011102955 | 12/2012 |
| DE | 102009058132 | 7/2014 |
| DE | 202008018523 | 4/2015 |
| DE | 102013106031 | 7/2015 |
| DE | 102012107175 | 8/2015 |
| DE | 102012102844 | 3/2020 |
| DE | 102019121546 | 2/2021 |
| DE | 102019121554 | 2/2021 |
| EP | 0836450 | 4/1988 |
| EP | 0902704 | 3/1999 |
| EP | 1003422 | 5/2000 |
| EP | 1295563 | 3/2003 |
| EP | 1441649 | 8/2004 |
| EP | 1483009 | 12/2004 |
| EP | 1494619 | 1/2005 |
| EP | 1527753 | 5/2005 |
| EP | 1569565 | 9/2005 |
| EP | 1574169 | 9/2005 |
| EP | 1054635 | 11/2005 |
| EP | 1610666 | 1/2006 |
| EP | 1633275 | 3/2006 |
| EP | 1651117 | 5/2006 |
| EP | 1659988 | 5/2006 |
| EP | 1725185 | 11/2006 |
| EP | 1804719 | 7/2007 |
| EP | 1862122 | 12/2007 |
| EP | 1923005 | 5/2008 |
| EP | 1923019 | 5/2008 |
| EP | 2063791 | 6/2009 |
| EP | 2134263 | 12/2009 |
| EP | 2157937 | 3/2010 |
| EP | 2207500 | 7/2010 |
| EP | 2244666 | 11/2010 |
| EP | 2265193 | 12/2010 |
| EP | 2266465 | 12/2010 |
| EP | 2279023 | 2/2011 |
| EP | 2324775 | 5/2011 |
| EP | 2349024 | 8/2011 |

(56) References Cited

FOREIGN PATENT DOCUMENTS

| | | |
|---|---|---|
| EP | 2367482 | 9/2011 |
| EP | 2387951 | 11/2011 |
| EP | 2399524 | 12/2011 |
| EP | 2460476 | 6/2012 |
| EP | 2468349 | 6/2012 |
| EP | 2496299 | 9/2012 |
| EP | 2506808 | 10/2012 |
| EP | 2543345 | 1/2013 |
| EP | 2567663 | 3/2013 |
| EP | 2596754 | 5/2013 |
| EP | 2613709 | 7/2013 |
| EP | 2617386 | 7/2013 |
| EP | 2618709 | 7/2013 |
| EP | 2647343 | 10/2013 |
| EP | 2677944 | 1/2014 |
| EP | 2744412 | 6/2014 |
| EP | 2848211 | 3/2015 |
| EP | 2854704 | 4/2015 |
| EP | 2887887 | 7/2015 |
| EP | 2923674 | 9/2015 |
| EP | 2926744 | 10/2015 |
| EP | 2943152 | 11/2015 |
| EP | 2964105 | 1/2016 |
| EP | 3068337 | 9/2016 |
| EP | 3082619 | 10/2016 |
| EP | 3131515 | 2/2017 |
| EP | 3136986 | 3/2017 |
| EP | 3148481 | 4/2017 |
| EP | 3151904 | 4/2017 |
| EP | 3171793 | 5/2017 |
| EP | 3187117 | 7/2017 |
| EP | 3247285 | 11/2017 |
| EP | 3261703 | 1/2018 |
| EP | 1998686 | 2/2018 |
| EP | 2460477 | 4/2018 |
| EP | 3345553 | 7/2018 |
| EP | 2806825 | 8/2018 |
| EP | 2753246 | 11/2018 |
| EP | 3413808 | 12/2018 |
| EP | 3429479 | 1/2019 |
| EP | 3456271 | 3/2019 |
| EP | 3456272 | 3/2019 |
| EP | 3501429 | 6/2019 |
| EP | 2254505 | 7/2019 |
| EP | 3510945 | 7/2019 |
| EP | 3512459 | 7/2019 |
| EP | 3517055 | 7/2019 |
| EP | 2194885 | 11/2019 |
| EP | 3572010 | 11/2019 |
| EP | 3173037 | 12/2019 |
| EP | 3574851 | 12/2019 |
| EP | 3585275 | 1/2020 |
| EP | 3600068 | 2/2020 |
| EP | 3622901 | 3/2020 |
| EP | 3628242 | 4/2020 |
| EP | 3636173 | 4/2020 |
| EP | 2405820 | 6/2020 |
| EP | 3669800 | 6/2020 |
| EP | 3677192 | 7/2020 |
| EP | 3714812 | 9/2020 |
| EP | 3153114 | 11/2020 |
| EP | 3740138 | 11/2020 |
| EP | 3755276 | 12/2020 |
| EP | 3501428 | 4/2021 |
| EP | 3568088 | 4/2021 |
| EP | 3808284 | 4/2021 |
| FR | 3061647 | 6/2020 |
| IL | 248515 | 7/2019 |
| JP | H02150481 | 6/1990 |
| JP | H0447415 | 4/1992 |
| JP | H08507011 | 7/1996 |
| JP | 2003-175113 | 6/2003 |
| JP | 2005028863 | 2/2005 |
| JP | 2005537092 | 12/2005 |
| JP | 2006509578 | 3/2006 |
| JP | 2010500187 | 1/2010 |
| JP | 2012-501793 | 1/2012 |
| JP | 2012030497 | 2/2012 |
| JP | 2013-027592 | 2/2013 |
| JP | 2013-509914 | 3/2013 |
| JP | 2013537069 | 9/2013 |
| RU | 2018131107 | 10/2018 |
| RU | 2019120682 | 9/2019 |
| RU | 2704539 | 10/2019 |
| RU | 2018145502 | 6/2020 |
| RU | 2018145543 | 6/2020 |
| RU | 2019110988 | 10/2020 |
| RU | 2019115837 | 11/2020 |
| RU | 2019116175 | 11/2020 |
| RU | 2019127900 | 3/2021 |
| RU | 2019129351 | 3/2021 |
| RU | 2019129526 | 3/2021 |
| WO | WO 2006/034149 | 3/2006 |
| WO | WO 2006/052322 | 5/2006 |
| WO | WO 2007/076480 | 7/2007 |
| WO | WO 2007/079402 | 7/2007 |
| WO | WO 2008/036156 | 3/2008 |
| WO | WO 2008/151204 | 12/2008 |
| WO | WO 2009/132045 | 10/2009 |
| WO | WO 2009/135166 | 11/2009 |
| WO | WO 2010/030991 | 3/2010 |
| WO | WO 2010/134914 | 11/2010 |
| WO | WO 2011/057002 | 5/2011 |
| WO | WO 2012/032030 | 3/2012 |
| WO | WO 2012/034135 | 3/2012 |
| WO | WO 2012/099704 | 7/2012 |
| WO | WO 2012/099909 | 7/2012 |
| WO | WO 2012/099910 | 7/2012 |
| WO | WO 2012/113554 | 8/2012 |
| WO | WO 2012/135037 | 10/2012 |
| WO | WO 2012/163880 | 12/2012 |
| WO | WO 2013/005195 | 1/2013 |
| WO | WO 2013/016618 | 1/2013 |
| WO | WO 2013/025711 | 2/2013 |
| WO | WO 2013/028579 | 2/2013 |
| WO | WO 2013/103888 | 7/2013 |
| WO | WO 2013/109309 | 7/2013 |
| WO | WO 2013/152327 | 10/2013 |
| WO | WO 2013/184595 | 12/2013 |
| WO | WO 2014/029835 | 2/2014 |
| WO | WO 2015/095538 | 6/2015 |
| WO | WO 2015/160721 | 10/2015 |
| WO | WO 2015/166013 | 11/2015 |
| WO | WO 2015/184075 | 12/2015 |
| WO | WO 2015/187196 | 12/2015 |
| WO | WO 2016/107357 | 7/2016 |
| WO | WO 2016/118420 | 7/2016 |
| WO | WO 2016/137997 | 9/2016 |
| WO | WO 2017/106567 | 6/2017 |
| WO | WO 2017/139702 | 8/2017 |
| WO | WO 2017/156275 | 9/2017 |
| WO | WO 2017/161283 | 9/2017 |
| WO | WO 2018/051187 | 3/2018 |
| WO | WO 2018/130624 | 7/2018 |
| WO | WO 2018/156833 | 8/2018 |
| WO | WO 2018/175221 | 9/2018 |
| WO | WO 2019/143755 | 7/2019 |
| WO | WO 2019/165360 | 8/2019 |
| WO | WO 2020/139544 | 7/2020 |
| WO | WO 2020/150023 | 7/2020 |
| WO | WO 2020/190620 | 9/2020 |
| WO | WO 2020/190630 | 9/2020 |
| WO | WO 2020/190639 | 9/2020 |
| WO | WO 2020/243039 | 12/2020 |
| WO | WO 2021/028160 | 2/2021 |
| WO | WO 2021/028161 | 2/2021 |
| WO | WO 2021/051110 | 3/2021 |

OTHER PUBLICATIONS

Bosworth et al., "Gamma irradiation of electrospun poly(ϵ-caprolactone) fibers affects material properties but not cell response,"

(56) References Cited

OTHER PUBLICATIONS

Journal of Polymer Science Part B: Polymer Physics, Apr. 2012, pp. 870-876.
CA Office Action in Canadian Appln. No. 2,946,078, dated May 26, 2021, 4 pages.
CN Office Action in Chinese Appln. No. 201580035663.X, dated Aug. 1, 2018, 27 pages (with English Translation).
CN Office Action in Chinese Appln. No. 201780024233.7, dated Apr. 22, 2021, 6 pages (with English translation).
CN Office Action in Chinese Appln. No. 201780024233.7, dated Jul. 9, 2020, 20 pages (with English Translation).
CN Office Action in Chinese Appln. No. 201780024233.7, dated Oct. 22, 2020, 17 pages (with English Translation).
EP Extended Search Report in European Appln. No. 19159876.2, dated Jun. 14, 2019, 9 pages.
EP Extended Search Report in European Appln. No. 20201759.6, dated Nov. 12, 2020, 12 pages.
EP Office Action in European Appln No. 16808631.2, dated Aug. 16, 2019, 8 pages.
Izadi et al., "Teflon hierarchical nanopillars with dry and wet adhesive properties," Journal of Polymer Science Part B: Polymer Physics, Apr. 2012, pp. 846-851.
JP Office Action in Japanese Appln. No. 2018-529554, dated Nov. 30, 2020, 11 pages (with English translation).
JP Office Action in Japanese Appln. No. 2018-548075, dated Mar. 25, 2021, 8 pages (with English translation).
Ohta et al., "Size control of phase-separated liquid crystal droplets in a polymer matrix based on the phase diagram," Journal of Polymer Science Part B: Polymer Physics, Apr. 2012, pp. 863-869.
Popov et al., "Interacting nanoparticles with functional surface groups," Journal of Polymer Science Part B: Polymer Physics, Mar. 2012, pp. 852-862.
U.S. Appl. No. 14/699,188, filed Nov. 5, 2015.
U.S. Appl. No. 15/372,128, filed May 14, 2019.
U.S. Appl. No. 16/080,626, filed Aug. 28, 2018.
U.S. Appl. No. 16/172,157, filed Oct. 26, 2018.
U.S. Appl. No. 16/407,957, filed Sep. 5, 2019.
U.S. Appl. No. 16/590,821, filed Oct. 2, 2019.
U.S. Appl. No. 16/640,142, filed Feb. 19, 2020.
U.S. Appl. No. 16/952,756, filed Nov. 19, 2020.
JP Office Action in Japanese Application No. 2018-529554, dated Jul. 12, 2021, 6 pages (with English translation).
JP Office Action in Japanese Application No. 2018-529554, dated Sep. 15, 2020, 6 pages (with English translation).
JP Office Action in Japanese Application No. 2019-145966, dated Sep. 1, 2020, 6pages (with English translation).
PCT International Preliminary Report on Patentability in International Application No. PCT/EP2016/080152, dated Jun. 12, 2018, 10 pages.
PCT International Preliminary Report on Patentability in International Application No. PCT/EP2017/055765, dated Sep. 11, 2018, 9 pages.
PCT International Written Opinion in International Application No. PCT/EP2021/054103, dated Aug. 26, 2021, 4 pages.
Altes et al., "Creation of Saccular Aneurysms in the Rabbit: A Model Suitable for Testing Endovascular Devices," AJR Am J Roentgenol. 2000, 174(2):349-354.
Blackshear et al., "Appendage obliteration to reduce stroke in cardiac surgical patients with atrial fibrillation," Ann. Thorac. Surg., Feb. 1996, 61(2):755-9.
CN Office Action in Chinese Appln. No. 201780024233.7, dated Jul. 9, 2020, 15 pages (with English Translation).
Gottlieb et al., "Anticoagulation in atrial fibrillation. Does efficacy in clinical trials translate into effectiveness in practice?" Arch. Intern. Med., Sep. 1994, 154(17):I945-53.
JP Office Action in Japanese Appln. 2017-508761, dated Nov. 27, 2018, 4 pages (English translation).
JP Office Action in Japanese Appln. No. 2017-508761, dated Mar. 19, 2019, 3 pages (English translation).
PCT Form ISA/206—Invitation To Pay Additional Fees in International Appln. PCT/EP2016/080152, dated Feb. 24, 2017, 9 pages.
PCT International Preliminary Report on Patentability in International Application No. PCT/EP2015/059429, dated Jul. 13, 2016, 11 pages.
PCT International Preliminary Report on Patentability in International Appln. No. PCT/EP2019/072576, dated Feb. 25, 2020, 12 pages.
PCT International Search Report and Written Opinion in International Application No. PCT/EP2016/080152, dated Jun. 16, 2017, 8 pages.
PCT International Search Report and Written Opinion in International Appln. No. PCT/EP2018/072576, dated Nov. 21, 2018, 20 pages.
PCT International Search Report and Written Opinion in International Appln. PCT/EP2015/059429, dated Jul. 6, 2015, 5 pages.
PCT International Search Report in International Appln. PCT/EP2017/055765, dated Apr. 18, 2017, 5 pages.
Schaffer. "Biocompatible Wire." Advanced Materials & Processes, Oct. 2002, pp. 51-54.

\* cited by examiner

CLOT REMOVAL DISTAL PROTECTION METHODS

FIELD OF THE INVENTION

The invention disclosed herein relates generally to the field of clot removal protection devices and/or clot removal protection device systems and/or implantable devices for the use of clot removal protection.

BACKGROUND OF THE DISCLOSURE

There is a significant demand for the development of emboli protection devices for safer removal of clot material in patients suffering from an ischemic stroke event. Currently there is an unmet need for such devices which would provide a means of offering a protection barrier while preventing clinical sequelae that may lead to longer term morbidity and long-term patient rehabilitation. Safer removal of a clot contributes to a reduction in healthcare costs associated with treating patients impacted by ischemic stroke. While proximal protection devices are used in carotid arteries, no such devices are capable of offering protection deeper in the neurovascular bed, particularly for delivery distally in the brain.

Therefore, the invention methods disclosed herein adapt an implantable device design used for aneurysm and vessel occlusion treatment to an innovative treatment technique for deep brain and/or vessel embolic protection. See aneurysm treatment/occlusion device in U.S. Pat. No. 10,130,372, incorporated herein by reference in its entirety.

All documents and references cited herein and in the referenced patent documents, are hereby incorporated herein by reference.

SUMMARY OF THE INVENTION

Disclosed herein is a method for protecting distal vessels from emboli that dislodged during clot aspiration or mechanical thrombectomy using an emboli protection device which functions as a mesh shield thereby trapping emboli which can be retrieved and removed through an aspirating catheter.

In one embodiment, the method for protecting distal vessels from emboli comprises advancing an aspiration catheter to a position proximal to a clot burden, delivering through the aspiration catheter a microcatheter over a guidewire through to the distal end of a clot burden in a vessel to be treated, removing the guidewire, delivering and deploying an emboli protection device via an exchange length delivery wire through the microcatheter and placing the deployed device distal to the clot burden until it fully opposes the vessel wall creating a circumferential seal across the vessel, removing the microcatheter and leaving the emboli protection device and the exchange length delivery wire in place in the vessel, loading an aspiration catheter over the exchange length delivery wire and advancing the aspiration catheter proximal to the clot burden, commencing aspiration of the clot, whereby aspiration causes vulnerable clot emboli to become dislodged and trapped in the emboli protection device.

In one embodiment of the method disclosed herein, an emboli protection device is an implantable device comprising: (a) a substantially solid marker having a proximal end, and a distal end; and (b) a resilient mesh body attached to the distal end of the marker, the body having a delivery shape and a deployed shape capable of conforming to vessel walls; wherein the body is a dual layer of resilient mesh folded over onto itself to create a circumferential fold line around the circumference of the body, and folded over ends of the resilient mesh, and wherein all of the folded over ends of the dual layer of mesh are within the marker.

In another embodiment, the substantially solid marker is attached to an exchange length delivery wire. In one embodiment, the marker cannot be detached from the exchange length delivery wire. i.e. is permanently attached to the delivery wire.

In further embodiments, of the method disclosed herein, additional or varied steps include, without limitation, advancing the aspiration catheter through the clot, using a guidewire inside the aspiration catheter to navigate a large bore lumen device into position, and/or pulling back/while removing the emboli protection device and continuing to aspirate, whereby ensuring all trapped emboli are safely removed from the vessel.

In another embodiment of the method disclosed herein, an emboli protection device is an implantable device comprising: (a) a substantially solid marker having a proximal end, and a distal end; and (b) a resilient mesh body attached to the distal end of the marker, the body having a delivery shape and a deployed shape capable of conforming to vessel walls; wherein the body has a diameter greater than a diameter of a vessel to be treated. In another embodiment, the resilient mesh body has a low profile height to width ratio. In another embodiment, the height of the resilient mesh body is between about 10-20% of its width.

In another embodiment, the resilient mesh body of the device is a dual or double layer mesh. In a further embodiment, the dual layer of mesh comprises a single layer of mesh folded circumferentially.

In another embodiment, the proximal end of the marker of the emboli protection device is attached to an exchange length delivery wire.

In further embodiments, the marker is a radiopaque marker, the marker comprises a rigid member, and/or the marker is a solid ring.

Also disclosed herein is a kit comprising the emboli protection device disclosed herein and a delivery means for deploying the device.

In other embodiments, the device in the preceding paragraphs may incorporate any of the preceding or subsequently disclosed embodiments.

The Summary of the Invention is not intended to define the claims nor is it intended to limit the scope of the invention in any manner.

Other features and advantages of the invention will be apparent from the following Drawings, Detailed Description, and the Claims.

DETAILED DESCRIPTION

The invention disclosed herein is illustrated in the drawings and description in which like elements are assigned the same reference numerals. However, while particular embodiments are illustrated in the drawings, there is no intention to limit the invention to the specific embodiment or embodiments disclosed. Rather, the invention disclosed herein is intended to cover all modifications, alternative constructions, and equivalents falling within the spirit and scope of the invention. As such, the drawings are intended to be illustrative and not restrictive.

Unless otherwise defined, all technical terms used herein have the same meaning as commonly understood by one of ordinary skill in the art to which this technology belongs.

Exemplary embodiments of the invention disclosed herein are depicted in FIGS. 1-10.

Exemplary embodiments of the invention disclosed herein and in FIGS. 1-10 are as follows:
15: device in delivery shape
20: device in deployed shape
26: circumferential fold line
28: coil wound core of EDW
30: dual layer resilient mesh
32: height of mesh
40: vessel
50: marker
60: clot burden
70: microcatheter
80: guidewire
90: aspiration catheter
100: embolic material
110: exchange delivery wire
120: dovetail portion of exchange delivery wire For the purposes of the invention disclosed herein, the terminology "corresponds to" means there is a functional and/or mechanical relationship between objects which correspond to each other. For example, an embolic protection device delivery system corresponds to (or is compatible with) an embolic protection device for delivery and deployment thereof.

For the purposes of the invention disclosed herein, the terminology "emboli protection device" or "distal protection device" means and/or may be interchangeable with terminology such as, without limitation, "device" or "device system" or "device implant" or "implant" and the like.

As disclosed herein the term "low profile" means that the resilient mesh body, in free air, has a height that is between about 10-20% of its width.

The invention disclosed herein is a method of protecting vessels distal or downstream of a clot (60) obstruction while the clot (60) is being removed from the brain or in a vessel (40) elsewhere in the body. Typically, as a clot is removed by either mechanical thrombectomy or aspiration, small fragments of clot can dislodge and travel downstream causing further obstruction and clinical sequelae. The invention disclosed herein utilizes a emboli protection device (15) as disclosed herein which is delivered and deployed (20) distal to the clot burden (60) by navigating a small catheter (70) through the clot burden (60) in the vessel (40) with minimal disruption to the clot (60). As the clot burden (60) is being removed, the deployed device (20) functions to protect the distal vessels from the risk of vulnerable embolic material (100) dislodged from the clot burden (60). The emboli protection device (20) is constructed with a double (or dual) layer of resilient mesh (30) which opens into a cup-like structure in which the resilient mesh opposes the vessel (40) circumferentially, thereby trapping any dislodged clot debris (100) during aspiration of the clot burden (60) or, alternatively, during mechanical thrombectomy. Once the clot burden (60) has been removed, the device (20) comprising trapped debris (100) in the device's resilient mesh body, is pulled back (away from or in the opposite direction of the distal vasculature) to the opening of the aspiration catheter (90) so that the trapped debris (100) gets aspirated at the same time the device is being pulled into the catheter (90) lumen.

Disclosed herein is a method for protecting distal vessels from emboli (100) that dislodged during clot aspiration using a device (20) which functions as a mesh shield thereby trapping emboli (100) which can be retrieved and removed through an aspirating catheter (90). The methods disclosed herein utilize a device (20) which is constructed from a woven resilient mesh material, the ends of which originate and terminate within a substantially solid marker, such as a radiopaque marker, at which point, affixed thereto is an exchange length delivery wire (110) for advancement of the device to a target site.

The invention method disclosed herein requires the use of an emboli protection device (20) whose body is comprised of resilient mesh folded (back onto itself) circumferentially in such as manner so as to create a mesh shield for trapping and removing any and all vulnerable emboli (100) from a vessel (40) comprising a clot burden (60). In one embodiment, the emboli protection device (20) body is a dual layer of resilient mesh (30) folded over onto itself to create a circumferential fold line around the circumference of the body, and folded over ends of the resilient mesh, and wherein all of the folded over ends of the dual layer of mesh are within the marker. See aneurysm treatment/occlusion device in U.S. Pat. No. 10,130,372, incorporated herein by reference in its entirety.

In one embodiment, the method for protecting distal vessels from emboli comprises a) advancing an aspiration catheter to a position proximal to a clot burden and delivering through the aspiration catheter a microcatheter (70) over a guidewire (80) through to the distal end of a clot burden (60) in a vessel (40) to be treated, b) removing the guidewire (80), c) delivering and deploying an emboli protection device (20) through the microcatheter (70) and placing the device (20) distal to the clot burden (60) until it fully opposes the vessel (40) wall creating a circumferential seal across the vessel (40), wherein the emboli protection device (20) is attached to an exchange length delivery wire (110), d) removing the microcatheter (70) and leaving the emboli protection device (20) and the exchange length delivery wire (110) in place in a distal location to the clot burden (40), e) commencing aspiration of the clot (60), whereby aspiration causes vulnerable clot emboli (100) to become dislodged and trapped in the emboli protection device (20).

In another embodiment, the method for protecting distal vessels from emboli comprises additional or varied steps which include, without limitation, g) advancing the aspiration catheter (90) through the clot (60), h) using a guidewire (80) inside the aspiration catheter (90) to navigate a large bore lumen device into position, and/or i) pulling back/while removing the emboli protection device (20) and continuing to aspirate, whereby ensuring all trapped emboli (100) are safely removed from the vessel (40).

In one embodiment of the emboli protection device (20) disclosed herein, the position of the distal end of the substantially solid marker (50) is attached approximately centrally on the underside of the resilient mesh body, that is, the marker (50) opposes the folded over mesh at the top side of the device (20). Such a positioning of the marker on the mesh body confers full connection capability to the exchange length delivery wire (110) of the device (20) used in the methods disclosed herein. In one embodiment, the device (20) cannot be detached from the exchange delivery wire (110) because the exchange delivery wire (110) is attached to the device via its dovetail portion (120) residing within the marker (50). See FIG. 2. In another embodiment, all the folded over ends of the resilient mesh are within the marker (50). See FIG. 2. In another embodiment, all the folded over ends of the dual layer of resilient mesh (30) originate and terminate in the marker (50). See FIG. 2. In another embodiment, the emboli protection device (20) used herein is "oversized" relative to a vessel (40) comprising a clot burden (60) to be treated. In this instance, the diameter (x) of the device (20) is greater than the diameter of any vessel (40) containing a clot burden (60) to be treated so long as the body of the device (20) is capable of conforming to vessel (40) walls by opposing the vessel (40) walls to create a circumferential seal across the vessel (40).

In one embodiment, the emboli protection device (20) disclosed herein is constructed of DFT Nitinol (NiTi) (DFT=Drawn Filled Tubing) to permit recovery of the device to its preformed disc like configuration, ensuring that when it is deployed it expands to oppose the vessel (40) circumferentially thereby trapping any vulnerable and dislodged clot debris (100). In one embodiment, the number of wires of the device construction ranges from 24 to 32 wire ends, double backed on each other to create a double layer of resilient mesh to give the equivalent of 48 to 64 strands in the resilient mesh body of the device. In one embodiment, the body of the device is relatively flat or curved to create a cup like appearance in the vessel (40) and this confers a protective barrier once the device (20) opposes the vessel (40) wall.

In one embodiment, the embolic protection device (20) disclosed herein is the vessel implantation device disclosed in U.S. Pat. No. 10,130,372, incorporated herein by reference in its entirety. In another embodiment, the device disclosed herein is similar to the vessel implantation device disclosed in U.S. Pat. No. 10,130,372, except the device used herein for protecting distal vessels from dislodged emboli (100) does not have a detachment point between the device marker (50) and the end of the exchange delivery wire (110). Instead, the device (20) is attached and cannot be detached from the exchange delivery wire (110). In one embodiment, the device (20) cannot be detached from the exchange delivery wire (110) because the exchange delivery wire (110) is attached to the device via its dovetail portion (120) residing within the marker (50). In one embodiment, the exchange delivery wire has a diameter of about 0.014 inches. The appropriate diameter is determined to ensure sufficient bond strength between the device (20) and the exchange delivery wire (110) as it is being retrieved inside the aspiration catheter (90) in the final steps of the methods disclosed herein.

The methods disclosed herein provide protection deeper in the neurovascular bed (that is, for example, deeper into the brain in the more distal vasculature beyond the clot burden) because of the unique construction of the emboli protection device (20) for use in the methods but additionally because of the distal placement of the device in relation to the clot burden (60). The emboli protection device (20) disclosed herein is scalable to treat larger vessels and its particular construction of resilient mesh with ends originating and terminating in the marker (50), combined with its low profile delivery (15) and deployment (20) shapes, uniquely confer the capability to be delivered deeper distally in the brain in the distal vasculature beyond the clot burden. In particular, the device (20) disclosed herein is flexible enough to conform to vessels (40) of varying diameters ranging from as small as about 2.5 mm up to about 4 mm in diameter.

For the purposes of the emboli protection device (20) and methods of use disclosed herein, the terminology "low profile" means that the resilient mesh body, in free air, has a height (32) that is between about 10-20% of its width, and therefore in its deployed shape the resilient mesh body of the device (20) is capable of conforming to vessel (40) walls by opposing the vessel (40) walls to create a circumferential seal across the vessel (40). In another embodiment of the device (20) used in the methods disclosed herein, the single layer or dual layer (30) of resilient mesh material of the device comprises a relatively uniform distribution of wire mesh strands or braids such as, without limitation, a 32 nitinol (NiTi) wire mesh strand braided configuration. In other embodiments, the device comprises wire mesh strands or braids that range from 24 to 64 NiTi strand braided configuration. In another embodiment, the number of wires of the device construction ranges from 24 to 32 wire ends, double backed on each other to create a double layer of resilient mesh to give the equivalent of 48 to 64 strands in the resilient mesh body of the device. In one embodiment, the body of the device is relatively flat or curved to create a cup like appearance in the vessel (40) and this confers a protective barrier once the device (20) opposes the vessel (40) wall.

In another embodiment, an embolic protection device (20) disclosed herein is a configuration of wire mesh which is folded circumferentially (circumferential fold line (26)) and therefore doubled back on itself to create a dual layer of resilient mesh (30). The ends of the dual or doubled back layer (30) intersect with the marker (50) positioned approximately at the core of the body of the device (20). In this regard, the device is constructed by circumferentially folding a single layer of mesh material over itself on a preferential (or circumferential) fold line effectively resulting in a device (20) comprising a dual layer (30) of wire mesh material, i.e., the dual layer of mesh (30) comprises a single layer of mesh folded circumferentially (circumferential fold line (26)). The doubled or dual layer (30) of wire mesh material contributes to the enhanced acute thrombogenicity of the device (20) in prior animal studies. It is also believed that this provides the device (20) with the capability, once deployed deep in the vasculature and distal to the clot burden (60), to fully oppose the vessel (40) wall creating a circumferential seal across the vessel (40).

In its low-profile deployed shape (20), the resilient mesh body, having a double backed dual layer (30) combined with its placement deeper in the vasculature when compared to a non-deployed (15) doubled back dual layer of resilient mesh accounts for a change in width of approximately 15% which translates to an increase in the diameter (x) of the device (20) when pressure is applied at the marker (50). This change in width/increase in diameter (x) is an effective anchoring feature of the deployed device (20) as blood applies pressure to the mesh body distributed across the vessel (40). Such a configuration also provides sufficient apposition of the mesh body of the device (20) against the vessel (40) wall.

FIGS. 1-10 show the position of the marker (50), having a proximal end and a distal end, on an emboli protection device (20) of the invention disclosed herein. In one embodiment, the distal end of the marker (50) is attached to the resilient mesh body of the emboli protection device (15, 20). In another embodiment, the proximal end of the marker (50) is affixed to and cannot be detached from the exchange length delivery wire (110). In another embodiment, the exchange delivery wire (110) is attached or affixed to the device (20) by a dovetail portion (120) end of the exchange delivery wire (110).

In one embodiment, the marker (50) of the device disclosed herein is a substantially solid collar or rigid member such as, without limitation a solid ring comprised of materials such as, without limitation, gold, platinum, stainless steel, and/or combinations thereof. In another embodiment, radiopaque materials such as, without limitation, gold, platinum, platinum/iridium alloy, and/or combinations thereof, can be used. Such a marker (50) provides visualization of the device (20) during delivery and placement. In one embodiment, the marker (50) is positioned centrally within the device (20) so that the proximal end of the marker (50) is connected to the exchange length delivery wire (110). The solid construction of the marker (50) helps confer stability to the device (20) within the vessel (40) and prevents movement or the transfer of forces through the resilient mesh body thereby preventing misplacement or accidental movement of the device (20). In one embodiment, the marker (50) is configured with a junction to cooperate and release from/attach or connect to a suitable corresponding delivery means such as, without limitation, a delivery microcatheter (70), catheter, exchange length delivery wire (110), guide wire (80) and/or pusher wire technologies.

In another embodiment, the substantially solid marker (50) comprises a radiopaque material (such as for example, without limitation, platinum, gold, platinum/iridium alloy, and/or combinations thereof) to facilitate visualization of the device (20) under fluoroscopy during delivery, placement and/or deployment. The marker (50) comprises a proximal end and a distal end. A resilient mesh body is attached to the distal end and the proximal end of the marker (50) may be configured to influence shape, diameter, and/or curvature of the resilient mesh body upon expansion of the device (20) disclosed herein. The marker (50) may be designed in various shapes to influence the overall profile of the emboli protection device (20) to ensure a proper fit of the expanded/deployed device (20) within the vessel (40).

Figure 1:
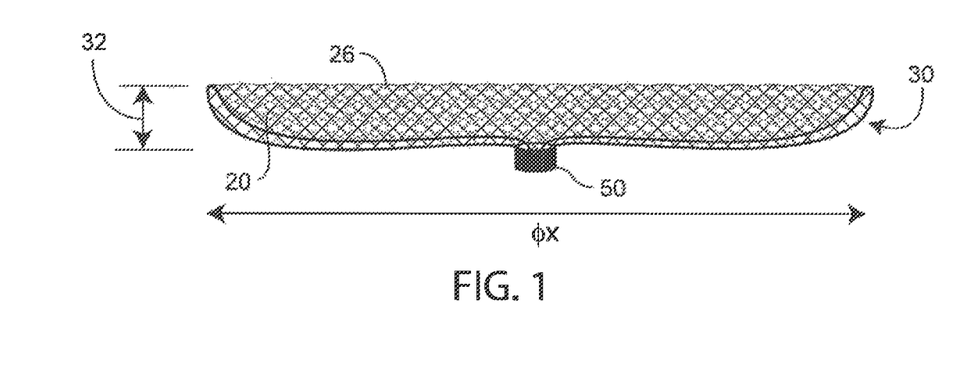
FIG. 1 illustrates a perspective view of an embodiment of the clot removal protection device disclosed herein and shows a low profile capability of the device relative to its diameter and height in free air.
Figure 2:
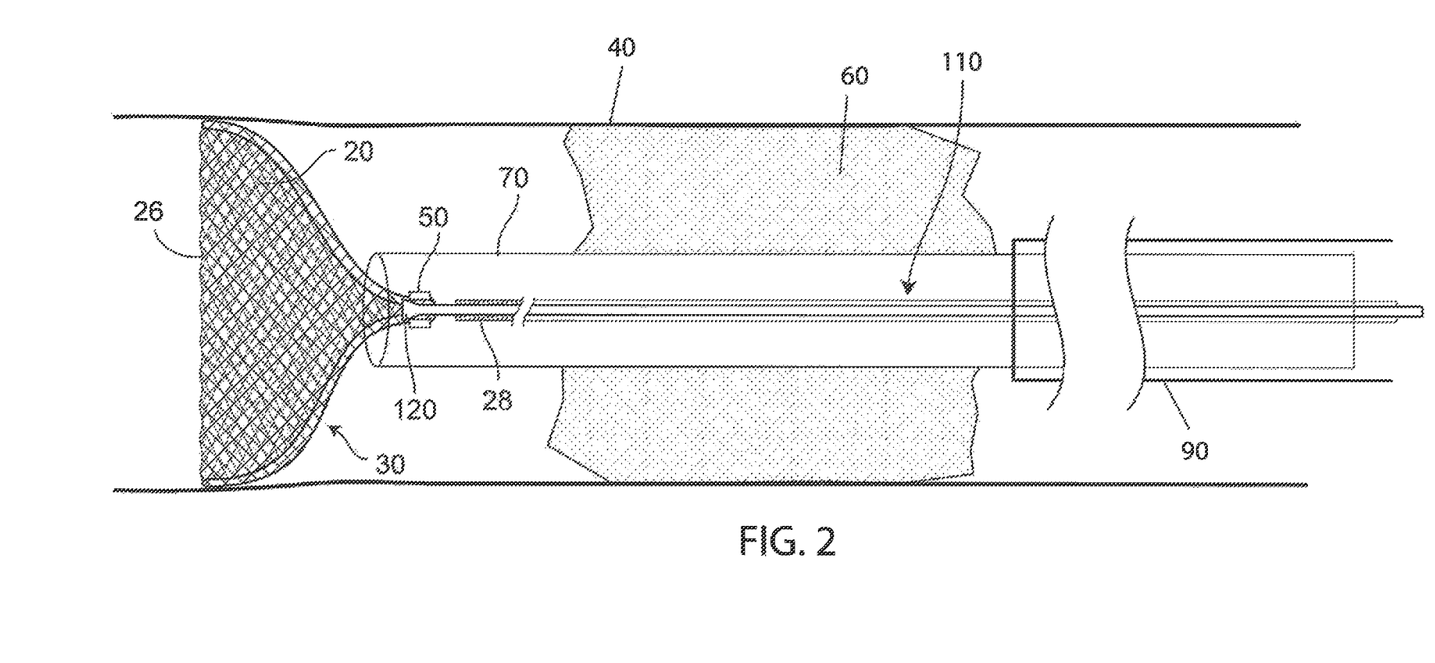
FIG. 2 illustrates a cross section perspective view of an embodiment of the clot removal protection device and shows both the embodiment of the ends of the dual layer of resilient mesh ending in the marker and the embodiment of the dovetail end of the exchange delivery inside the marker.
Figure 3:
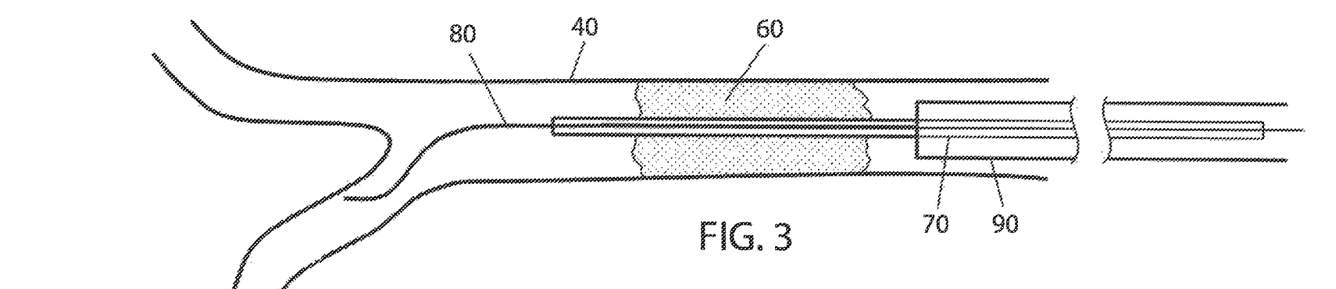
FIG. 3 illustrates a perspective view of an embodiment of an embolic protection method disclosed herein and shows advancement of an aspiration catheter for placement proximal to the clot burden and then the advancement of a microcatheter and a guidewire through the aspiration catheter located proximal to the clot burden and continuing advancement of the microcatheter through the clot burden to a distal position relative to the clot burden.
Figure 4:
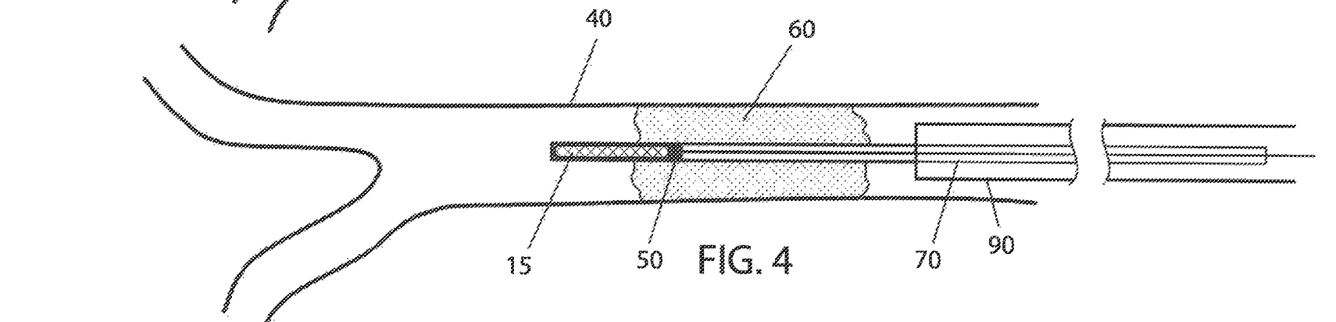
FIG. 4 illustrates a perspective view of an embodiment of an embolic protection method disclosed herein and shows the guidewire removal and the emboli protection device delivery advancement through the microcatheter to a location distal to the clot burden.
Figure 5:
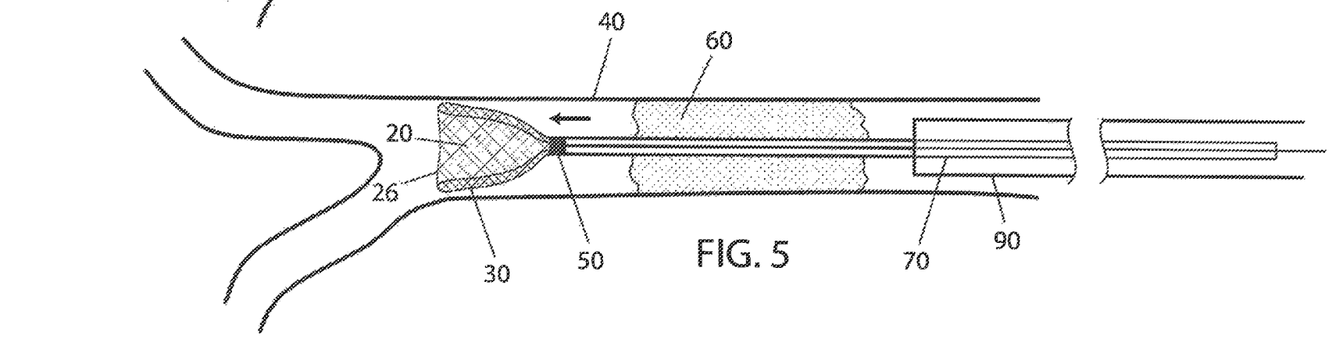
FIG. 5 illustrates a perspective view of an embodiment of an embolic protection method disclosed herein and shows the emboli protection device deployment distal to the clot burden as it begins to open and oppose the vessel wall to create a circumferential seal across the vessel.
Figure 6:
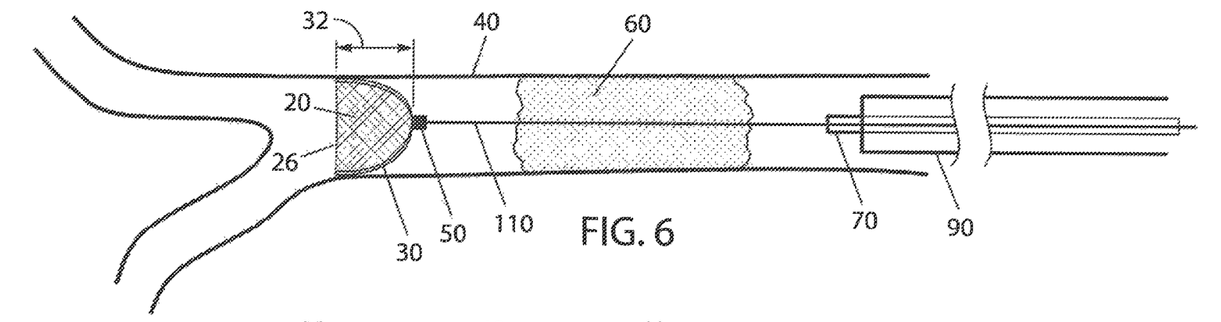
FIG. 6 illustrates a perspective view of an embodiment of an embolic protection method disclosed herein and shows the removal of the microcatheter over the exchange delivery wire leaving the emboli protection device (attached to the exchange delivery wire) in place in a distal location to the clot burden.
Figure 7:
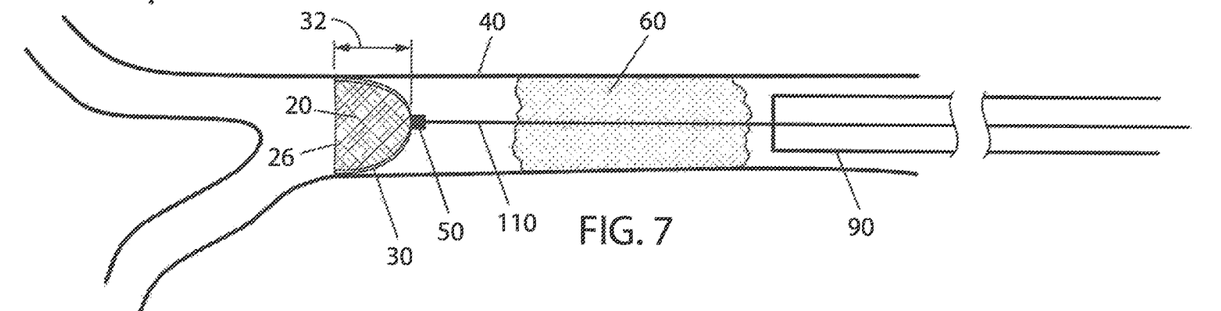
FIG. 7 illustrates a perspective view of an embodiment of an embolic protection method disclosed herein and shows the aspiration catheter in a location proximal to the clot burden for the commencement of aspiration.
Figure 8:
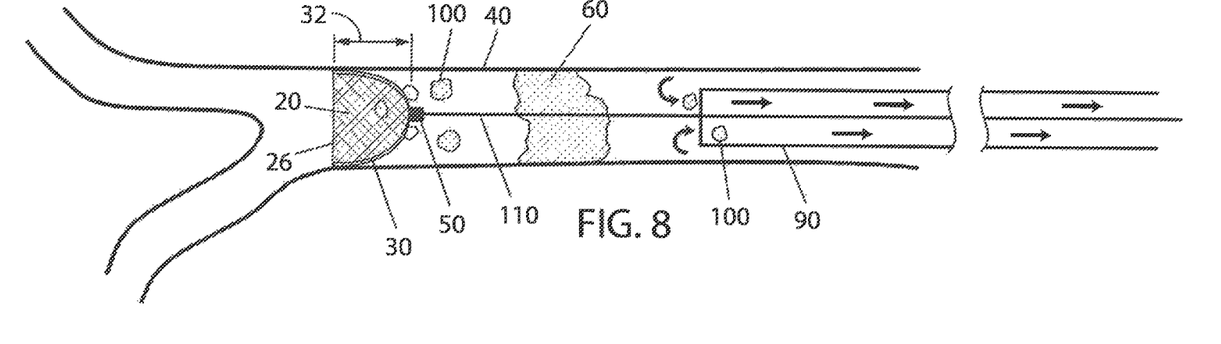
FIG. 8 illustrates a perspective view of an embodiment of an embolic protection method disclosed herein and shows the clot burden being aspirated while vulnerable clot emboli become dislodged and trapped in the emboli protection device.
Figure 9:
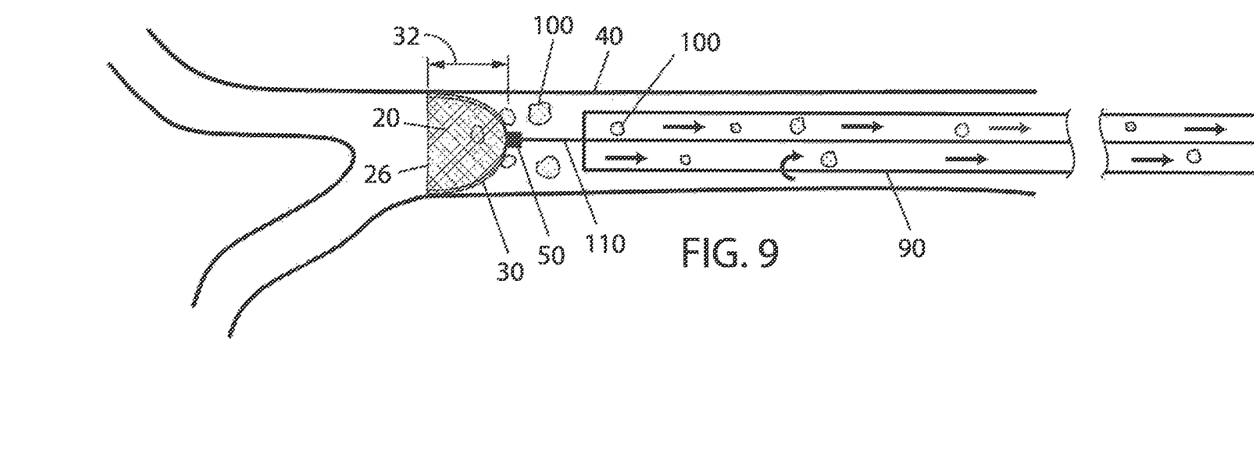
FIG. 9 illustrates a perspective view of an embodiment of an embolic protection method disclosed herein and shows continuation of the aspiration of the clot burden and emboli while vulnerable clot emboli become dislodged and trapped in the emboli protection device.
Figure 10:
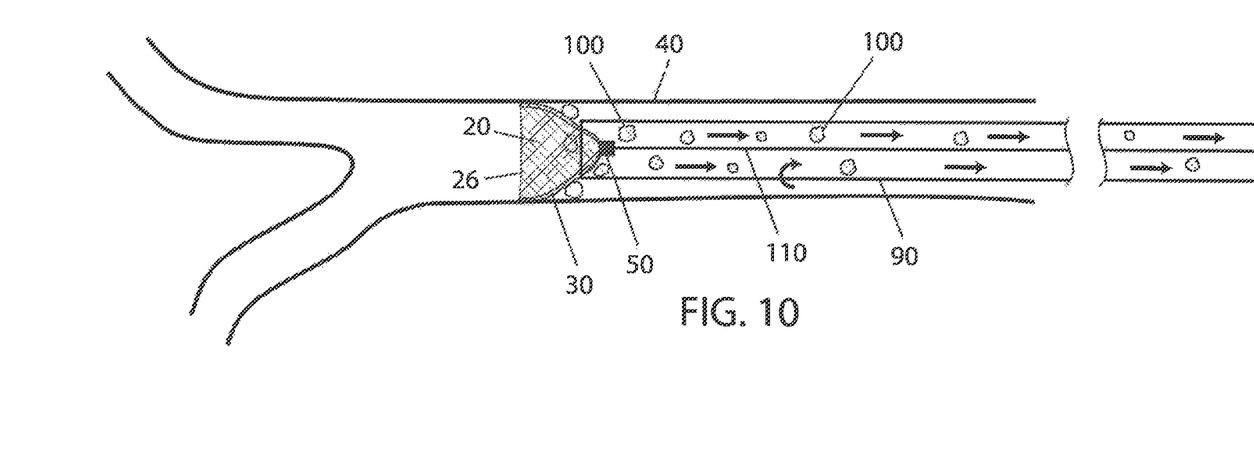
FIG. 10 illustrates a perspective view of an embodiment of an embolic protection method disclosed herein and shows the combination of pulling the emboli protection device back inside the aspiration catheter while continuing to aspirate for the purpose of ensuring all trapped emboli are safely removed from the vessel.

FIGS. 2-10 show an exemplary method for delivery and/or deployment, through a clot burden within a vessel. In one embodiment, the device (15) is delivered in a closed, compacted position (delivery shape) as shown in FIGS. 3 and 4, such that the low profile resilient mesh body is closed inward on itself or compressed, via a pusher wire mechanism in a microcatheter (70). When the device (20) is pushed into and/or placed in a distal location relative to the clot burden (60), the ends of the low profile resilient mesh body open outward in the manner of the opening of a cup-like configuration with the cup's open end facing opposite or away from the clot (60) (as shown in FIGS. 5-9) and the opened body then conforms to the walls of the vessel (40) and fully opposes the vessel walls creating a circumferential seal across the vessel (40). In one embodiment, as shown in FIGS. 6-8, the device (20) comprising its dual layer of resilient mesh (30) is capable of deepening or increasing its depth accounting for a change in width and an increase in the diameter of the device (20) when pressure is applied at the marker (50). This change in width/increase in diameter is an effective anchoring feature of the deployed device (20) as blood applies pressure to the resilient mesh (30) body distributed across and sealing the vessel (40) distal to the clot burden (60). Results of animal studies provided herein support that the circumferential seal created by the cup-like configuration of the dual layer of resilient mesh (30) provides efficient apposition of the mesh body against the vessel (40) wall.

In other embodiments, the device (20) disclosed herein may further incorporate separate or combined adjunctive elements and/or members such as coiling techniques, framing coils, embolic agents, additional markers, polymers, resorbent polymers and/or a combination thereof.

Resilient mesh materials for design and/or manufacture of the device disclosed herein are readily available and well known by those skilled in the relevant art. As such, resilient mesh materials range from a wide variety of available materials such as, without limitation, nickel titanium (nitinol or otherwise known as NiTi), stainless steel, polymers, and/or combinations thereof. Exemplary known biomedical polymeric families include, without limitation, polymers such as polyphosphazenes, polyanhydrides, polyacetals, poly(ortho esters), polyphosphoesters, polycaprolactones, polyurethanes, polylactides, polycarbonates, polyamides, and/or a combination thereof. (See, e.g., J Polym Sci B Polym Phys. Author manuscript; available in PMC 2012 Jun. 15.)

In one exemplary embodiment, the resilient mesh material is formed of woven strands of polymer material, such as, without limitation, nylon, polypropylene or polyester. The polymer strands can be filled with a radiopaque material which allows the physician treating the aneurysm to fluoroscopically visualize the location of the device within the vasculature. Radiopaque filler materials preferably include bismuth trioxide, tungsten, titanium dioxide or barium sulfate, or radiopaque dyes such as iodine. The resilient mesh material can be formed by strands of radiopaque material. The radiopaque strands allow the physician and/or radiologist to fluoroscopically visualize the location of the mesh, without the use of filled polymer materials. Such radiopaque strands may be formed with materials such as, without limitation, gold, platinum, a platinum/iridium alloy, and/or a combination thereof. In one embodiment, the resilient mesh material is constructed of 10%-20% platinum core NiTi. In another embodiment, the resilient mesh material is constructed of 10% platinum core NiTi, 15% platinum core NiTi, or 20% platinum core NiTi. 10% platinum core NiTi construction is sufficient to provide a ghost image of the device under x-ray.

Such constructed combination wires or composite wires having a radiopaque core and non-radiopaque outer layer or casing are readily available and well known in the medical device and metallic arts as DFT® (drawn-filled-tube) wires, cables or ribbons. DFT® wire is a metal-to-metal composite constructed to combine the desired physical and mechanical attributes of two or more materials into a single wire. By placing the more radiopaque, but more ductile material in the core of the wire, the NiTi outer layer is able to provide the resulting composite wire with similar mechanical properties of a 100% NiTi wire. DFT® wires are available from Fort Wayne Metals Corp., Fort Wayne, Ind., U.S.A. See also, for example, the journal article entitled Biocompatible Wire by Schaffer in Advanced Materials & Processes, October 2002, pages 51-54, incorporated herein by reference.

Where the resilient mesh material is formed of radiopaque metal strands, the strands may be covered with a polymer coating or extrusion. The coating or extrusion over the radiopaque wire strands provides fluoroscopic visualization but also increases the resistance of the strands to bending fatigue and may also increase lubricity of the strands. The polymer coating or extrusion, in one embodiment, is coated or treated with an agent which tends to resist clotting, such as heparin. Such clot resistant coatings are generally known. The polymer coating or extrusion can be any suitable extrudable polymer, or any polymer that can be applied in a thin coating, such as Teflon® or polyurethane.

In yet another embodiment, the strands of the resilient mesh material are formed using both metal and polymer braided strands. Combining the metal strands with the polymer strands into a braid changes the flexibility characteristics of mesh. The force required to deploy and/or collapse such a mesh portion is significantly reduced over that required for a mesh portion that includes only metal mesh strands. However, the radiopaque characteristics of the mesh for fluoroscopic visualization are retained. Metal strands forming such a device includes, without limitation, stainless steel, gold, platinum, platinum/iridium, nitinol, and/or combinations thereof. Polymer strands forming the device can include nylon, polypropylene, polyester, Teflon®, and/or combinations thereof. Further, polymer strands of the mesh material can be chemically modified to make them radiopaque with known techniques such as, without limitation, by using gold deposition onto the polymer strands, or by using ion beam plasma deposition of suitable metal ions onto the polymer strands.

The resilient mesh material can also be formed with filaments or strands of varying diameter and/or varying flexibility. By varying the size or flexibility of the polymer strands, the flexibility characteristics of the mesh, upon deployment, can also be varied. By varying the flexibility characteristics, both the deployed and collapsed configuration of the resilient mesh body can be varied or changed to substantially any desired shape.

Not only can the mesh be formed of both polymer strands or filaments and metal strands or filaments, but it can be formed using filaments of different polymer materials. For example, different polymer materials having different flexibility characteristics can be used in forming the mesh. This alters the flexibility characteristics to change the resultant configuration of the mesh body in both the deployed and the collapsed positions. Such biomedical polymers are readily known and available in the art and can be derived from polymeric families such as, without limitation, polyphosphazenes, polyanhydrides, polyacetals, poly (ortho esters), polyphosphoesters, polycaprolactones, polyurethanes, polylactides, polycarbonates, polyamides, and/or a combination thereof.

Resilient mesh materials suitable for use within the mesh body may take the form of a flat woven sheet, knitted sheet, or a laser cut wire mesh. In general, the material should include two or more sets of substantially parallel strands, with one set of parallel strands being at a pitch of between 45 degrees and 135 degrees with respect to the other set of parallel strands. In some embodiments, the two sets of parallel strands forming the mesh material are substantially perpendicular to each other. The pitch and general construction of the mesh material may be optimized to meet the performance needs of the device.

The wire strands of the metal fabric used in the invention disclosed herein should be formed of a material which is both resilient and can be heat-treated to substantially set a desired shape. Materials which are believed to be suitable for this purpose include a cobalt-based low thermal expansion alloy referred to in the field of medical devices as Elgiloy®, nickel-based high-temperature high-strength "superalloys" commercially available from Haynes International under the trade name Hastelloy®, nickel-based heat treatable alloys sold under the name Incoloy® by International Nickel, and a number of different grades of stainless steel. The important factor in choosing a suitable material for the wires is that the wires retain a suitable amount of the deformation induced by the molding surface (or shape memory, as described below) when subjected to a predetermined heat treatment.

One class of materials which meet these qualifications are so-called shape memory alloys. Such alloys tend to have a temperature induced phase change which will cause the material to have a preferred configuration which can be fixed by heating the material above a certain transition temperature to induce a change in the phase of the material. When the alloy is cooled, the alloy will "remember" the shape it was in during the heat treatment and will tend to assume that same and/or similar configuration unless constrained from doing so.

One particular shape memory alloy for use in the invention disclosed herein is nitinol, an approximately stoichiometric alloy of nickel and titanium, which may also include other minor amounts of other metals to achieve desired properties. NiTi alloys such as nitinol, including appropriate compositions and handling requirements, are well known in the art and such alloys need not be discussed in detail here. For example, U.S. Pat. Nos. 5,067,489 and 4,991,602, the teachings of which are incorporated herein by reference, discuss the use of shape memory NiTi alloys in guide wire-based technologies. Such NiTi alloys are preferred, at least in part, because they are commercially available and more is known about handling such alloys than other known shape memory alloys. NiTi alloys are also very elastic. Indeed, they are said to be known as "superelastic" or "pseudoelastic." This elasticity will help an emboli protection device (20) as disclosed herein return to prior expanded configuration for deployment thereof.

In some embodiments, the wire strands comprise a standard monofilament of the selected material, i.e., a standard wire stock is used. In some embodiments, 24 wire strands and/or 24 strand braid configurations are used. In other embodiments, the device comprises wire mesh strands or braids that range from 24 to 48 NiTi strand braided configurations. If so desired, though, the individual wire strands may be formed from "cables" made up of a plurality of individual wires. For example, cables formed of metal wires where several wires are helically wrapped about a central wire are commercially available and NiTi cables having an outer diameter of 0.003 inches or less can be purchased. One advantage of certain cables is that they tend to be "softer" than the monofilament wires having the same diameter and formed of same material. Additionally, the use of a cable increases the effective surface area of the wire strand, which will tend to promote thrombosis.

An emboli protection device (20) disclosed herein is configured with low profile resilient mesh material of a mesh density sufficient for functioning in such a manner as an endothelial cell scaffold within a vessel. For the purposes of the invention disclosed herein, the terminology "mesh density" means the level of porosity or the ratio of metal to open area of the mesh body. Mesh density relates to the number and size of the openings or pores of the mesh and by the extent that the pores are open or closed in situations where opening or pore openness varies between delivery and deployment. Generally, a high mesh density region of a resilient mesh material has approximately about 40% or more metal area and about 60% or less open area.

In some embodiments, the resilient mesh body of the device (20) is formed uniformly of the same material; however such material may have different knitted, stitched, braided, and/or cut construction.

The principal use of aspiration catheters is to remove a thrombus that forms in a patient's arteries to prevent obstruction of the blood vessel in which the thrombus has formed due to a stroke or blockage. Aspiration catheters (90) used in the distal protection methods herein are readily available in the art. Aspiration catheters (90) usually consist of an over the wire single lumen system with a distal radiopaque tip marker and a proximal luer lock port attached to a syringe for hand-powered suction or a mechanical/aspiration pump to remove a thrombus. The catheter further includes an aspiration port to which a source of negative pressure is attached. In one embodiment, the aspiration catheter (90) is approximately 95-135 cm in length. Suction in aspiration catheters can be provided by an apparatus such as a pump, e.g., a vacuum pump, or a syringe. In some embodiments, the aspiration catheter (90) is a large bore aspiration catheter. In some embodiments, the aspiration catheter (90) is an aspiration pump. An aspiration catheter used in the distal protection methods disclosed herein is an aspiration catheter of a standard size. Radiopaque markers can be located at the distal ends of the catheters to assist in positioning the catheter within the body. Aspiration catheters are generally constructed with varying flexibility along the length of the shaft such that they are sufficiently flexible to be steered through the patient's vasculature without causing damage, but retain adequate stiffness to enable the axial push needed to place the catheter in the proper location and to withstand the aspiration pressures. Aspiration catheters used herein may vary in size, typically ranging from 5 thru 8 French (Fr.) (1 Fr.=0.013 inches). (As is well known in the art, the French scale or French gauge system is commonly used to measure the size of a catheter.)

Microcatheters (70) used herein are typically standard in sizing and readily available in the art. For example, microcatheter profiles such as the commonly used, 017 (internal diameter $17/1000$s inch), and the 021 are well known and readily available. In certain embodiments, a 017 microcatheter is small enough that when you advance it thru the clot burden (60) the clinician (or operator) creates minimal disturbance of the clot (60)—i.e., prevents disturbance of the clot burden (60). Microcatheters used herein are selected based upon criteria such as anatomy, vessel size, pressure variances, capability to preclude trauma, and system compatibility.

The device (20) and methods disclosed herein may incorporate reasonable design parameters, features, modifications, advantages, and variations that are readily apparent to those skilled in the art in the field of medical devices.

EXAMPLES

An animal study was conducted to evaluate the mechanics of the procedure and the interaction of the device with other devices used in the clot aspiration procedure. The study was conducted in the Research Institute of Neurointervention, Animal Lab, Salzburg, Austria under supervision of a veterinarian and experienced Neurointerventional Radiologists.

Clot doped with Tantalum for ease of visualization was prepared and introduced into the animal vasculature.

The first step of the clot removal distal protection procedure was to advance nn 0.014" guidewire through the clot burden, followed by advancing the microcatheter to the distal end of the clot. The microcatheter was then strategically positioned to deploy the embolic protection device distal to the clot burden. Accordingly, the embolic protection device was advanced through the microcatheter and deployed distal to the clot burden. With the device successfully deployed and the microcatheter in place, the aspiration catheter was advanced over the microcatheter into position proximal to the clot burden. The microcatheter was then removed over the exchange length wire of the embolic protection device prior to aspirating the clot.

The clot was successfully aspirated via two methods:

The distal protection device remained in place while the clot was being aspirated and the aspiration catheter was advanced up to the device and finally pulled inside the lumen removing all collected emboli that dislodged during aspiration.

After approximately 50% of the clot burden was aspirated, the operator pulled the distal protection device proximally, pulling the remaining clot burden inside the aspiration catheter while still applying suction.

The device used in this study was delivered through an 021 microcatheter, similar to what stentrievers are delivered through for mechanical thrombectomy. The optimal device configurations are variable according to each patient to be treated. In one embodiment, the distal protection device is delivered through an even smaller, e.g., 017, microcatheter to minimize the disturbance of the clot burden when advancing through the distal end of the clot to deploy the device. In another embodiment, the device is be constructed with 48 wire strands of 0.001" DFT Nitinol which will permit the operator to observe the device being successfully deployed and open beyond the clot.

In certain embodiments, the device configurations ranges in diameter from 2.5 to 4.5 mm and the size of the device will be selected depending on the size of the vessel it is being deployed into to offer good wall apposition and distal protection.

Manipulation and deployment control of the occlusion device were carried out while visualizing the proximal radiopaque marker of the device in relation to the catheter tip. Device development will entail the incorporation of radiopaque struts of platinum core NiTi wire to aid in visibility.

Device manipulation and deployment was easy to manipulate with pinpoint accuracy, particularly in relation to guidance through the vessels and the clot burden as well as placement of the device distal to the clot burden in the treated animals.

A number of embodiments of the invention have been described. Without departing from the scope and spirit of the invention disclosed herein, reasonable features, modifications, advantages, and design variations of the claimed apparatus will become readily apparent to those skilled in the art by following the guidelines set forth in the preceding detailed description and embodiments. Accordingly, other embodiments are within the scope of the following claims.

What is claimed is:

1. A method for protecting distal vessels from dislodged emboli comprising:
   a. advancing an aspiration catheter proximal to clot burden,
   b. advancing a microcatheter and guidewire through the aspiration catheter through and distal to the clot burden in a vessel to be treated,
   c. removing the guidewire,
   d. deploying an emboli protection device comprising a resilient mesh body through the microcatheter and placing the device distal to the clot burden until it fully opposes the vessel wall thereby creating a circumferential seal across the vessel, wherein the emboli protection device is attached to an exchange length delivery wire, wherein the exchange length delivery wire comprises a dovetail portion end inside a marker of the device,
   e. removing the microcatheter and leaving the emboli protection device and the exchange length delivery wire in place in the vessel, and
   f. commencing aspiration of the clot, whereby aspiration causes vulnerable clot emboli to become dislodged and trapped in the emboli protection device.

2. The method according to claim 1, wherein the emboli protection device is an implantable device comprising:
   a. the marker having a proximal end, and a distal end; and
   b. the resilient mesh body, wherein the resilient mesh body is attached to the distal end of the marker, wherein the resilient mesh body has a delivery shape and a deployed shape capable of conforming to vessel walls; wherein the resilient mesh body is a dual layer of resilient mesh folded over onto itself to create a circumferential fold line around the circumference of the body, and folded over ends of the resilient mesh, and wherein all of the folded over ends of the dual layer of mesh are within the marker.

3. The method according to claim 2, wherein the marker is attached to the exchange length delivery wire.

4. The method according to claim 1, further comprising g) advancing the aspiration catheter up to the clot as the aspiration catheter applies suction.

5. The method according to claim 4, further comprising h) the combination of pulling back while removing the emboli protection device and continuing to aspirate, whereby ensuring all trapped emboli are safely removed from the vessel.

6. The method according to claim 1, wherein the emboli protection device is an implantable device comprising: (a) the marker having a proximal end, and a distal end; and (b) the resilient mesh body attached to the distal end of the marker, the body having a delivery shape and a deployed shape capable of conforming to vessel walls; wherein the body has a diameter greater than a diameter of a vessel to be treated.

7. The method according to claim 1, wherein the resilient mesh body of the device has a low profile height to width ratio.

8. The method according to claim 7, wherein the resilient mesh body of the device has height that is between about 10-20% of its width.

9. The method according to claim 1, wherein the resilient mesh body of the emboli protection device is a dual or double layer mesh.

10. The method of claim 9, wherein the dual layer of mesh comprises a single layer of mesh folded circumferentially.

11. The method according to claim 1, wherein the proximal end of the marker of the emboli protection device is attached to the exchange length delivery wire in such a manner wherein the emboli protection device cannot be detached from the exchange length delivery wire.

12. The method according to claim 1, wherein the marker is a radiopaque marker.

13. The method according to claim 1, wherein the marker comprises a rigid member.

14. The method according to claim 1, wherein the marker is a solid ring.

15. A method for removing a clot burden from a blood vessel comprising:
   a. advancing an aspiration catheter to a position proximal to the clot burden,
   b. advancing a microcatheter and guidewire to a position distal to the clot burden in a vessel to be treated,
   c. removing the guidewire,
   d. placing an emboli protection device comprising a resilient mesh body in position in a location distal to the clot burden and fully opposing the vessel wall to create a circumferential seal across the vessel, wherein the emboli protection device is attached to an exchange length delivery wire, wherein the exchange length delivery wire comprises a dovetail portion end inside a marker of the device,
   e. removing the microcatheter and leaving the emboli protection device in place in the vessel, and
   f. commencing aspiration of the clot burden.

16. The method of claim 15, wherein the resilient mesh body of the device has height that is between about 10-20% of its width.

17. The method of claim 15, wherein the resilient mesh body of the device is a dual or double layer mesh.

18. The method according to claim 17, wherein the dual layer of mesh comprises a single layer of mesh folded circumferentially.

* * * * *